United States Patent [19]

Burgett et al.

[11] 4,294,817

[45] Oct. 13, 1981

[54] METHOD OF FLUORO IMMUNOASSAY

[75] Inventors: Michael W. Burgett, El Granada; Richard A. Harte, Redwood City, both of Calif.

[73] Assignee: International Diagnostic Technology, Inc., Santa Clara, Calif.

[21] Appl. No.: 943,314

[22] Filed: Sep. 18, 1978

Related U.S. Application Data

[63] Continuation-in-part of Ser. No. 854,613, Nov. 25, 1977, abandoned.

[51] Int. Cl.³ .................. G01N 33/58; G01N 33/54; G01N 21/25; G01N 1/28
[52] U.S. Cl. .................. 424/8; 23/230 B; 422/56; 422/57; 422/58; 424/1.5; 424/12; 424/13; 435/4; 435/5; 435/7
[58] Field of Search .................. 424/1, 7.8, 12, 13; 23/230 B; 422/56, 57, 58; 435/4, 5, 6, 7

[56] References Cited

U.S. PATENT DOCUMENTS

| | | | |
|---|---|---|---|
| 3,992,631 | 11/1976 | Harte | 424/12 X |
| 3,999,948 | 12/1976 | Deindoerfer | 23/230 B |
| 4,020,151 | 4/1977 | Bolz | 23/230 B X |
| 4,025,310 | 5/1977 | Bolz | 23/230 B |
| 4,056,724 | 11/1977 | Harte | 424/12 X |
| 4,067,959 | 1/1978 | Bolz | 23/230 B X |
| 4,125,372 | 11/1978 | Kawai | 23/230 B |
| 4,133,639 | 1/1979 | Harte | 424/8 X |
| 4,135,884 | 1/1979 | Shen | 23/230 B |
| 4,163,779 | 8/1979 | Harte et al. | 424/8 X |

FOREIGN PATENT DOCUMENTS 2652091 5/1977 Fed. Rep. of Germany ... 195/103.5 V

OTHER PUBLICATIONS

Traganos et al., The J of Histochem & Cytochem, vol. 24, No. 1, 1976, pp. 40–48.
Toussaint et al., Applied Microbiol., vol. 13, 1965, pp. 552–558.
Hull, Lab World, vol. 29, Nov. 1978, pp. 79–83.
Clinical Chemistry, vol. 22, No. 4, Apr. 1976, Adv. 1 p.
Stewart, New Eng J Med, vol. 276, 1967, pp. 254–257.
Parkman, PSEBM, vol. 111, 1962, pp. 225–230.
Brown, Science, vol. 145, 28 Aug. 1964, pp. 943–945.
Schaeffer, Bacti Reviews, vol. 28, 1964, pp. 402–408.
Kalimo, J Clin Microbiol., vol. 4, No. 2, 1976, pp. 117–123.
Meurman, J Clin Microbiol., vol. 5, No. 3, 1977, pp. 257–262.
Voller, Br. J. exp. Path., vol. 56, 1975, pp. 338–339.
Miller, Clin Obs. Gyn., vol. 18, No. 1, 1975, pp. 191–203.
Kelen, Can. J Microbiol., vol. 8, 1962, pp. 545–554.
Plotkin, Rubella Virus, Diagnostic Proc. for Viral & Rickett. Infections, APhA, 1969, (Lennette et al. Ed), pp. 364–413.

*Primary Examiner*—Anna P. Fagelson
*Attorney, Agent, or Firm*—Limbach, Limbach & Sutton

[57] ABSTRACT

A new surface immunoassay method is performed with two test surfaces. The method is used where serum samples may contain both an antibody for which it is desirable to test, and also competing sera constituents which may be present in indeterminate amounts. In accordance with the method, two different test surfaces are contacted with the same serum sample, and preferably the same aliquot of the serum. The first surface is treated to bind a broad spectrum of serum components including both the component to be tested for and also the competing components. The second surface is designed to bind the competing components but no substantial amount of the serum component to be tested for. The immunoassay is conducted with a labeled antibody, and quantitative measurement of the immunoassay is obtained by detecting the quantitative difference in the amount of labeled antibody on the two surfaces which have been subjected to the same serum sample.

The method has utility in detecting a wide variety of antibodies of both the immunoglobulin G and immunoglobulin M classes, including antibodies for rubella, treponema, herpes simplex virus, cytomegalovirus and toxoplasma.

Preferably the two surfaces used in the test are mounted on a single sampler which is analyzed in the FIAX® Fluorometer.

14 Claims, No Drawings

METHOD OF FLUORO IMMUNOASSAY

RELATED APPLICATIONS

This is a continuation-in-part or our prior application, Ser No. 854,613 filed Nov. 25, 1977, abandoned.

BACKGROUND OF INVENTION

Rubella is usually a mild childhood disease of short duration. It would be of little importance were it not for the severe birth defects which result from congenital rubella infection during the first trimester of pregnancy. Thus, the determination of the immune status of individuals is important as a means of preventing these birth defects. Serological determinations of rubella are used to determine the immune status of individuals in a given population (particularly women of child bearing age) so that those unprotected can be vaccinated. The determinations also are used to evaluate the status of pregnant women who have been exposed to rubella so that they can be counseled as to the possibility of congenital infections. Finally, the serological determination of rubella serves as a diagnostic tool for the identification of the cause of exanthematous (rash causing) diseases.

A number of methods are currently available for the detection of antibodies to rubella virus. The most common are the hemagglutination inhibition assay (HI), the serum neutralization assay, the complement fixation assay (CF), and the indirect immunofluorescent assay (IF).

Certain viruses, including rubella, having the ability to combine with and agglutinate red blood cells (hemagglutination). When antibodies to rubella combine with the virus, they prevent the agglutination of the red blood cells. Stewart, et al. New Eng. J. Med. 276:554 (1967), used these properties of the rubella virus to develop the hemagglutination inhibition assay. Since the HI assay was first described, many variations in the procedure have been presented. This has prompted the Center for Disease Control (CDC) to offer a standardized method, Standardized Rubella Hemagglutination-Inhibition Test. Immunology Series No. 3, U.S.D. H.E.W., CDC, Atlanta, Ga. 30333, Oct. 1970.

The serum neutralization assay for rubella, which was first described by Parkman et al., Proc. So. Exp. Biol. Med. 3:225 (1962), is based upon the fact that viruses which are combined with antibodies are no longer infective.

A complement fixation assay has also been described for rubella, Lennette, E. H. in Diagnostic Procedures for Viral and Rickettsial Diseases, 3rd Ed. American Public Health Association, 1–66 (1964). This is based upon the ability of the antibody-rubella complex to bind (fix) complement.

Brown et al., Science 145:943 (1964), and Schaeffer, et al., Bact. Rev. 28:402 (1964) developed an indirect immunofluorescent assay for rubella. In this assay cells which were infected with rubella were fixed on slides. The fixed cells were incubated with diluted serum samples. Rubella antibodies in the sample combine with the rubella antigens in the fixed cells. The rubella antibodies on the cells are detected with a fluorescently labeled anti-human immunoglubulin antibody.

While these tests for rubella are known, they suffer from a number of disadvantages because of their clinical complexity, expense, time consumption and quantitative reliability and for this reason it is desirable to develop a new rubella test in which rubella can be detected through fluoro immunoassay rapidly and economically with dependable quantitative results.

A number of developments have been made in recent years in the art of fluoro immunoassay where patients may be tested for a particular component of a bodily fluid by (a) binding to a support surface a known sample of the component, (b) contacting the support surface with a sample of the bodily fluid to be tested so that antibodies in the bodily fluid may be attracted to the component on the support surface, (c) contacting the surface with a fluorescent tagged second antibody to the first antibody and (d) measuring the fluorescence of the resulting surface.

A number of technologies and instruments have been developed as indicated, for instance, in the following patents by which fluoro immunoassay has achieved a new level of quantitative consistency and convenience.

U.S. Pat. No. 3,992,631—Inventor: Richard A. Harte

U.S. Pat. No. 3,999,948—Inventors: Fred H. Deindoefer, et al

U.S. Pat. No. 4,020,151—Inventors: Gunner Bolz, et al.

U.S. Pat. No. 4,025,310—Inventors: Gunner Bolz, et al.

U.S. Pat. No. 4,056,724—Inventor: Richard A. Harte

Adapting these new fluoro immunoassay techniques and devices to a rubella test is a very desirable end result but produces substantial difficulties in attempting to obtain reliable quantitative results. Apparently, there are many competing substances interfering with the normal immunoassay procedures when these procedures are applied to rubella.

SUMMARY OF THE INVENTION

In accordance with this invention a fluoro immunoassay has been developed for anti-rubella antibodies employing some of the new techniques and devices for surface fluoro immunoassay mentioned above. The new test consists of a number of features taken in combination and additionally a double surface method which is broadly new in this art.

Thus, in accordance with this invention a double surface method has been developed for surface immunoassay with a viral antigen directly bound to the test surface. Likewise, we have found that we can perform a surface immunoassay with antigenic extracts of bacteria or protozoans bound to the test surface whereas heretofore immunoassays of this type were performed only with whole organisms.

The new two surface test makes immunoassays possible which heretofore had been impossible by cancelling out competing reactions. While the mechanism by which the reactions in the assay progress may not be fully understood, it is believed that fluoro immunoassay for anti-rubella antibodies is complicated by competing reactions with immunoglobulins or other serum components. These competing reactions are isolated from the final result of the assay by a new method in which two test surfaces instead of one progress together through every stage of the assay where the first surface binds the object of the assay, anti-rubella antibodies, as well as the competing proteins which otherwise interfere with reliability of the assay while the second surface binds those competing proteins but binds substantially none of the object of the assay. In accordance with the new method, the two test surfaces which go through the assay together are finally analyzed quantitatively for a tagging material preferably fluorescense and the result of the assay is taken as the difference between the fluorescence measurements on the two surfaces.

The two test surfaces may be prepared in a variety of ways, but preferably and for manufacturing convenience, the two test surfaces are prepared from the same materials with the test surfaces supported on a sampler by which the surfaces may be transferred through the assay. The test surfaces are preferably prepared in accordance with the procedure of the abandoned application of Naomi Kameda, Ser. No. 848,403, filed Nov. 4, 1977, and abandoned, Feb. 25, 1980. The test surface is preferably made of a porous copolymer to which the test material (rubella virus antigen) will bind upon drying. A suitable copolymer surface is a material available on the market under the tradename Millipore which is a copolymer of cellulose nitrate and cellulose acetate. The following materials may also be used as supports under specific conditions:

Hydrocarbon polymer such as polystyrene, polyethylene, polypropylene, polybutylene, butyl rubber and other synthetic rubbers, silastic rubber, polyesters, polyamides, cellulose and cellulosic derivatives, acrylates, methacrylates, and vinyl polymers such as vinyl chloride, and polyvinyl fluoride. Copolymers such as graft copolymers of polystyrene are also useful. In addition to the foregoing materials, the solid support surface may comprise silica gel, silicone wafers, glass, insoluble protein, and metallic surfaces (e.g., tantalum coated glass).

The second surface may be bound with another immunologically active analyte (i.e., control antigen from uninfected cells) which binds the competing blood serum proteins, such as lipoproteins and immunoglobulins but we have found that in the particular test for anti-rubella antibodies described herein, the second test surface may be the same material, Millipore, as the rubella virus test surface without any protein material initially bound to it.

As indicated above, the two test surfaces are preferably mounted on samplers which facilitate transfer of the test surfaces throughout the assay. Preferably, both of the test surfaces are mounted on a single sampler for additional ease in transferring the test surfaces through the assay, and this is particularly advantageous in the present anti-rubella test where an uncoated surface is used as a second surface since the processing steps for binding a rubella virus to the first test surface do not complicate preparation of the second test surface. The anti-rubella test surface of this invention is prepared with the intensive drying and prewashing features of the above-mentioned invention of Naomi Kameda, and in the present invention, additional advantages are obtained by conducting the intensive drying step under substantial refrigeration, that is, at temperatures within the range of about zero to 10° C. and preferably 2° to 6° C.

The novel sampler of this invention in which viral antigen is bound to a polymeric support may be used advantageously in immunoassay other than the assay of the specific examples which follow; for instance, radio immunoassay or enzyme tagged assay techniques instead of fluoro immunoassay. Additionally, the novel samplers of this invention with viral antigen bound to a polymeric support may be made with antigens from viruses other than rubella virus, for example, Herpes simplex virus I, and cytomegalovirus. (Also the material can be used with antigens from protozoan parasites, *Toxoplasma gondii*. Finally, it will be apparent that the novel method of this invention in which two surfaces are subjected to the same treatment, including incubation with an unknown serum sample and measurement of the difference in the amount of tagging material on the two surfaces, may be used in a wide variety of immunoassay tests to obtain consistent results despite the presence of interfering materials in the unknown serum sample. By way of example, an immunoassay can be performed for the quantitative identification in sera of antibodies against the syphilis causing bacterium *Treponema pallidum* as indicated in one of the examples which follows.

Once the test surfaces have been prepared, the assay is performed by sequentially moving the pair of test surfaces through (a) a diluted serum sample to be tested for anti-rubella antibodies, (b) a washing solution of buffered saline, (c) a buffered saline containing fluorescently labeled anti-human immunoglobulins, and finally, (d) a final wash solution. The two surfaces are then measured for the quantitative presence of the fluorescent labeling material preferably employing a FIAX ™ 100 Fluorometer of International Diagnostic Technology, Inc. The fluorescent measurements of the two surfaces are subtracted to give a difference measure. Finally, the difference measurement is compared to a plot of the difference measurements obtained from control serum solutions containing known quantities of identified anti-rubella antibodies, and if properly programed, the FIAX ®[1] Fluorometer with microcomputer accessory may perform these calculations.

FIAX is the registered trademark of International Diagnostic Technology, Inc. which was granted on Sept. 26, 1978 as Registration No. 1,102,995. The method may be varied in a number of ways as is known in the fluoro immunoassay art, but the method as specifically performed in the following illustrative specific example has been found to produce repeatable commercially satisfactory results.

EXAMPLE 1

PREPARATION OF SAMPLERS

In the following example, test samplers were prepared containing a circular disc 6.6 millimeters in diameter of Millipore type HAMK which is a copolymer of cellulose nitrate and cellulose acetate sold as an exclusion filter material rated for exclusion of particles over 0.45 microns. A large number of the samplers were prepared in the following way:

A commercially available rubella antigen solution was used in the preparation of the samplers. An acceptable material had to have a hemagglutination titer using one day old chick erythrocytes as the indicator cells of greater than 1:128 and a protein concentration of less than 11 mg/ml. Rubella Diagnostic HI antigen (lot C96 1290) purchased from Flow Laboratories, Rockville, Md. met these criteria and was used below.

A quantity of 25 microliters of the antigen solution was applied to each of the samplers. The wet samplers were placed in a drying chamber at 0° to 10° C. Other experiments indicate that temperatures of 0°–25° C. gave acceptable results. The drying chamber was maintained dry by maintaining a quantity of Drierite brand calcium chloride in the chamber which was replaced every twenty-four (24) hours.

The samplers were maintained in the chamber for forty-eight (48) hours at which time the samplers had come to equilibrium with the drying air at a relative humidity of less than about ten percent (10%). The samplers were then removed from the drying chamber.

A wash solution was prepared containing 0.05 Molar Tris (hydroxymethyl) aminomethane buffer at pH 8.6 l with 0.15 Molar sodium chloride, 0.1% NaN₃ and 0.35% Tween 20. The dried samplers were soaked for ten (10) minutes in the washing solution and then washing solution was shaken off the samplers which were returned to the dryer and dried for eighteen (18) hours at which time they were dry to visual inspection.

EXAMPLE 2

FLUORO IMMUNOASSAY

A washing buffer solution was prepared with 0.35% Tween 20 (polyoxyethylene sorbitan monolaurate) added to Tris (hydroxymethyl) aminomethane buffered saline and stored refrigerated. A dilution buffer solution was prepared containing 0.35% (polyoxyethylene sorbitan monolaurate) Tween 20 and 2.5% bovine serum albumin in Tris (hydroxymethyl) aminomethane buffered saline, and four calibration solutions I through IV were prepared from recalcified and delipidated human plasma with known titers by rubella hemagglutination inhibition assay. The approximate rubella titer of each calibrator is given in the chart below:

| Calibrator | Approximate Rubella Titer (The inverse of the highest dilution giving hemmagglutination inhibition) |
|---|---|
| I | 512 |
| II | 64 |
| III | 10 |
| IV | 5 |

A test tube rack was provided with 12×75 culture tubes. One milliliter of dilution buffer was added to the tubes in the first row and 1 milliliter of washing buffer to the second and fourth rows. In the tubes of the third row was placed 1 milliliter of a fluorescent reagent consisting of fluorescein isothiocyanate labeled goat antibody to human immunoglobulins diluted with Tris buffered saline at pH 8.4 with 2.5% bovine serum albumin and 0.35% Tween 20. In the first row of tubes, a 25 microliter aliquot of unknown sample or calibrator was added to each tube, one tube used for each of the calibrators and one tube used for each of the serum tests.

The test tube rack was placed on a horizontal shaker at room temperature with the test tubes mounted at 45° so that the tubes were agitated throughout the assay.

The samplers prepared above were placed in the first row of tubes with each tube containing one surface with bound rubella virus antigen and one control surface and the samplers were permitted to remain for thirty minutes under agitation. The samplers were then moved to the tubes of the second row and permitted to shake for five minutes to wash from the test surfaces any excess serum components which were not bound to the test surfaces. The samplers were then moved to the third row of tubes and permitted to shake for thirty minutes while any anti-rubella antibodies on the samplers and any competing serum proteins were permitted to react with the fluorescent labeled anti-human immunoglobulins. Finally, the samplers were transferred to the fourth row of tubes and permitted to shake ten minutes for a final wash. At each transfer, both the anti-rubella bound surface and the control surface were transferred so that a pair of test surfaces went through each test tube.

The test surfaces processed as described above were then measured for fluorescent material on a FIAX 100 Fluorometer and the results obtained thereby are recorded as follows where FSU indicates fluorescent signal units of the Fluorometer:

A Typical Experiment:

Assay performed as indicated in kit insert:

| Sample (ID No.) | Rubella Surface Sampler/ FSU | Control Surface Sampler/ FSU | Δ FSU | (A) FIAX Titer (Two Surface) | (B) FIAX Titer (Only Rubella Sampler) | (C) HAI Titer |
|---|---|---|---|---|---|---|
| Cal. I | 100 | 25 | 75 | — | — | 1024 |
| Cal. II | 69 | 26 | 43 | — | — | 320 |
| Cal. III | 56 | 23 | 32 | — | — | 64 |
| Cal. IV | 32 | 24 | 8 | — | — | 16 |
| 1(R 140) | 25 | 35 | −10 | <5 | 6.5 | <8 |
| 2(R 142) | 29 | 31 | − 2 | <5 | 9.5+ | <8 |
| 3(R 143) | 22 | 26 | − 4 | <5 | 5.0 | <8 |
| 4(R 144) | 30 | 33 | − 3 | <5 | 10.0+ | <8 |
| 5(R 145) | 33 | 40 | − 7 | <5 | 14.0+ | <8 |
| 6(R 146) | 25 | 33 | − 8 | <5 | 6.5 | <8 |
| 7(R 161) | 38 | 23 | 15 | 20 | 20.0 | 16 |
| 8(R 162) | 39 | 26 | 13 | 17 | 22.0 | 16 |
| 9(R 165) | 53 | 32 | 21 | 34 | 60.0+ | 32 |
| 10(R 167) | 39 | 22 | 17 | 24 | 22.0 | 32 |
| 11(R 178) | 52 | 24 | 28 | 60 | 68.0 | 64 |
| 12(R 179) | 46 | 21 | 25 | 47 | 40.0 | 64 |
| 13(R 195) | 64 | 26 | 38 | 145 | 190.0 | 128 |
| 14(R 196) | 49 | 25 | 24 | 42 | 54.0 | 128 |

(A) Values determined from a standard curve produced by plotting HAI titer vs. Δ FSU  Δ FSU = FSU (Rubella StiQ® Sampler) - FSU (Control StiQ® Sampler).
(B) Values determined from a standard curve produced by plotting HAI titer vs. FSU (Rubella StiQ® Sampler).
(C) HAI titer: Titer determined by hemagglutination-inhibition (See Standardized Rubella Hemagglutiatnion-Inhibition Test; Immunology Series No. 2, USDHEW, Center for Disease Control, Atlanta, GA 30333, October 1970). Values are the reciprocal of the highest dilution of the serum sample which still inhibits hemagglutination. This test is considered the reference method for rubella determinations.
NOTE:
Samples 2, 4, 5 have false positive titers (>8 titer) with the single StiQ® method but have negative titer (<8) with the two StiQ® method. Also, there is a generally better agreement between FIAX and HAI titer with two StiQ® method than with the single StiQ® method.

EXAMPLE 3

TWO SURFACE METHOD WITH ANTI-TREPONEMA ANTIBODY

Samplers were prepared in a manner similar to that described above with active surfaces made of Millipore HAMK. One group of the samplers were spotted with a ten microliter aliquot of specially purified FTA-ABS antigen (Beckman Cat. No. 251041, Lot E6 00135) and dried at 0° to 8° C. for twenty hours at a relative humidity of less than ten percent (10%).

A group of samples were prepared by diluting reactive *Treponema pallidum* sera (i.e., sera containing antibodies to *Treponema pallidum*) and sera non-reactive with *Treponema pallidum* (i.e., sera containing no antibodies against *Treponema pallidum*). These diluted samples were prepared with normal rabbit serum. Further dilutions of the reactive and non-reactive sera were prepared with a buffer containing 0.05 M Tris HCl, pH 8.2, 0.15 M NaCl, 0.005 M EDTA, 0.1% Tween 20 and 2% bovine serum albumin.

These dilutions were made to provide the sample final dilution indicated below. A pair of one of each of the treated and untreated samplers was placed in each of the sera samples and shaken for thirty minutes. The samplers were then washed for ten minutes in a buffer solution and were then shaken for thirty minutes in a 1:50 dilution of FITC labeled rabbit anti-human immunoglobulin and finally washed for ten minutes. The two samplers were measured for fluorescent material on a FIAX 100 Fluorometer with the following results:

| Sample | Dilution | Antigen FSU | Control FSU | Δ FSU |
|---|---|---|---|---|
| Reactive | 1:10 | 56 | 30 | 26 |
| Reactive | 1:20 | 46 | 28 | 18 |
| Reactive | 1:40 | 37 | 28 | 9 |
| Non-Reactive | 1:10 | 89 | 120 | −31 |
| Non-Reactive | 1:20 | 52 | 61 | − 9 |
| Non-Reactive | 1:40 | 34 | 41 | − 7 |

By just using the antigen samplers, the non-reactive sera actually has higher fluorescence than the antigen samplers with reactive sera. The ΔFSU (the antigen sampler FSU less the blank sampler FSU) was much higher for the reactive sera than for the non-reactive sera.

EXAMPLE 4

TWO-SIDED SAMPLER

A series of tests were performed in the same manner as described above but with each unknown tested once with two samplers and a second time with a single sampler having the two test surfaces on opposite sides of the same sampler with the following results indicating that acceptable results are obtained with the two test surfaces on a single sampler:

| Sample | Expected Titer | Titer with Double Sided Sampler | Titer with 2 Samplers |
|---|---|---|---|
| 1 | <8 | <5 | <5 |
| 2 | <8 | <5 | <5 |
| 3 | <8 | 6 | 6 |
| 4 | <8 | 7 | 7 |
| 5 | <8 | 5 | 5 |
| 6 | <8 | 10 | 13 |
| 7 | <8 | 9 | 8 |
| 8 | <8 | 6 | 8 |
| 9 | 8 | 8 | 10 |
| 10 | 8 | 19 | 18 |
| 11 | 8 | 19 | 21 |
| 12 | 8 | 11 | 14 |
| 13 | 8 | 12 | 17 |
| 14 | 8 | 12 | 12 |
| 15 | 8 | 14 | 12 |
| 16 | 8 | 8 | 8 |
| 17 | 16 | 20 | 29 |
| 18 | 16 | 34 | 36 |
| 19 | 16 | 22 | 31 |
| 20 | 32 | 52 | 56 |
| 21 | 32 | 52 | 94 |
| 22 | 64 | 476 | 232 |
| 23 | 64 | 52 | 44 |
| 24 | 128 | 106 | 150 |
| 25 | 128 | 73 | 81 |
| 26 | 256 | 249 | 240 |
| 27 | 512 | 202 | 280 |

The test procedures were identical except that for each test with two samplers the serum sample used was 15 microliters of serum in 600 microliters of buffer while with the two sided sampler the serum sample used was 25 microliters of serum in 1000 microliters of buffer. Less solution can be used with the two-sided sampler while keeping the active surfaces covered by solution.

EXAMPLE 5

TWO SURFACE ASSAY FOR HERPES SIMPLEX VIRUS TYPE I (HSV-1) and CYTOMEGALOVIRUS (CMV)

A series of tests was performed to demonstrate that the method was useful for assay for HSV-1 and CMV. These tests were performed as described above using two samplers and serum samples diluted in buffer at a rate of 40:1. For the HSV-1 assays, the samplers were prepared as follows:

A circular disc 6.6 millimeters in diameter of Millipore type HAMK, copolymer of cellulose nitrate and cellulose acetate, was attached to a sampler by double sided adhesive tape and then a 25 microliter aliquot of a commercially available HV CF antigen (Flow Laboratories, Cat. No. 40-607-44, lot No. V948036) was spotted on the disc. As a control, a 25 microliter aliquot of HV CF tissue control antigen (Flow Laboratories, Cat. No. 41-607-44, lot No. V948035C) was spotted on the same type surface. Both antigen and control samplers were dried at 10% humidity at 0°-8° C. for 24 hours.

For the CMV assays, the samplers were prepared with similar discs, similarly attached to a sampler. On one surface, a 25 microliter aliquot of commercially available CMV CF antigen (Flow Laboratories, Cat. No. 40-613-44, lot No. W946078) was spotted on the surface and as a control a similar surface was spotted with a 25 microliter aliquot of CMV FC tissue control antigen (Flow Laboratories, Cat. No. 41-613-44, Lot No. W946078C). Again, both samplers were dried at 10% humidity at 0°-8° C. for 24 hours. Assays were performed as described in Examples 1 and 2. The results were compared to assays performed by hemagglutination inhibition method.

| Sample | HSV-1 | (HAI) | Double Sampler HSV-1 | CMV | (HAI) | Double Sampler CMV |
|---|---|---|---|---|---|---|
| 1 | 8, | <8 | 9 | 128, | 256 | 140 |
| 2 | 1024, | 2048 | 500 | 64, | 64 | 500+ |
| 3 | 256 | | 280 | 128, | 128 | 140 |
| 4 | 32, | 32 | 31 | 16, | 16 | 17 |
| 5 | 32, | 64 | 198 | 32, | 64 | 132 |
| 6 | <8, | <8 | 6 | <8, | <8 | 6 |
| 7 | 8, | 8 | 11 | <8, | <8 | 13 |
| 8 | 128, | 256 | 500 | <8 | | 8.5 |
| 9 | <8 | | 8 | 1024 | | 500+ |
| 10 | 256, | 128 | 210 | 64, | 128 | 500+ |
| 11 | 128 | | 90 | 16, | 32 | 48 |
| 12 | 128, | 256 | 210 | 16, | 32 | 16 |
| 13 | 32 | | 290 | 128 | | 310 |
| 14 | <8 | | 6.5 | <8 | | 7 |
| 15 | 8 | | 7 | 8 | | 7 |
| 16 | <8 | | 26 | 256 | | 500 |
| 17 | <8 | | 7.6 | <8 | | 7 |
| 18 | <8 | | 6 | <8 | | 50 |
| 19 | 128 | | 145 | 8, | 16 | 8.5 |
| 20 | 256 | | 500 | 128 | | 500 |
| 21 | 16 | | 11 | 256, | 512 | 500 |
| 22 | 16 | | 12 | NSR | | 8.5 |
| 23 | <8 | | 15 | 32 | | 170 |
| 24 | 128, | 256 | 310 | <8 | | 10 |
| 25 | 16, | 32 | 10 | 32 | | 7 |
| 26 | <8 | | <5 | <8 | | <2 |
| 27 | <8 | | <5 | <8 | | <2 |

EXAMPLE 6

TWO SURFACE METHODS FOR IgM AND IgG

A series of tests were conducted to estimate the concentration of IgM type anti-rubella antibodies in patients' serum over time. These assays were performed as described in Examples 1 and 2. For the IgG tests, the solution in the third test tube was fluorescein isothiocyanate (FITC) labeled goat anti-human IgG. For the IgM tests, the third test tube contained monospecific FITC labeled goat anti-human IgM. Additionally, for the IgM tests, the serum samples in test tube 1 were diluted 1:10.

Standardization for IgM was obtained by employing serum from a recent rubella infection as a high calibrator. The presence of IgM type antibodies was verified by the ELISA technique [Voller, A. and Bidwell, D. E. Brit. J. Exptl. Pathol. 57:243 (1976)]. Comparative tests were done on a number of serum samples from various patients testing for IgG as described in Examples 1 and 2 and testing for IgM in the same way as Example 1, but with the IgM antibody as indicated above, by the standard hemagglutination method. These samples also were tested by an IgG specific ELISA method and an IgM specific ELISA method. The results are tabulated as follows:

| Patient Sample and Time | HAI (Titer) | IgG (Titer) | IgG ELISA (μgm/ml) | IgM-ELISA (Log Absorb) | IgM (Titer) |
|---|---|---|---|---|---|
| P 8 days after immunization | <10 | 4.2 | | | 3.0 |
| P 11 days after immunization | <10 | 4.7 | | | 5.0 |
| P 27 days after immunization | 20 | 6.8 | | | 16.0 |
| P 34 days after immunization | 20 | 7.9 | | | 34.0 |
| M pre-immunization | <10 | 4.2 | | | 5.2 |
| M 27 days after immunization | 80 | 64.0 | | | 78.0 |
| R ¼ | 8(<4) | 3.8 | 22.4 | 2.4 | <2 |
| R 3/23 | 512 | 190.0 | 447 | 2.5 | 2.0 |
| W ¼ | 16 | 9.5 | 8.9 | 1.543 | 160 |
| W 3/23 | 128 | 40.0 | 141.2 | 0.865 | 60 |
| Ch ¼16/8 | 32 | 13.33 | 8.9 | 2.144 | 12 |
| Ch 3/22 64 | 128 | 11.16 | 89.0 | 1.202 | <2 |
| Ca 11/4 8 by CF | 32/64 | 27 | | | 12 |
| CA 11/14 | 32/64 | 22 | | | 10 |

The surface test method described above has also been employed for fluoro immunoassays for Epstein Barr virus and for toxoplasma.

EXAMPLE 7

TOXOPLASMA

A series of tests were performed to demonstrate the use of the two surface method for fluoro immunoassays for toxoplasma. This test was performed substantially as described in Examples 1 and 2, except that the two samplers for each assay were prepared as follows:

A circular disc 6.6 millimeters in diameter of Millipore, HAMK, copolymer of cellulose nitrate and cellulose acetate was attached to a sampler by double side adhesive tape. A 10 microliter aliquot of soluble Toxoplasma gondii antigen prepared by the method of Walls, et al. [K. W. Walls, S. L. Bullock, and D. K. English, J. Clin. Microbiol. 5:273 (1977)] was spotted on the disc. The samplers were dried at about 10% humidity at 0°–8° C. for 24 hours. Untreated samplers were used as a control.

A group of serum samples were assayed by the method of Kelen et al. (Kelen, A. E., Ayllon-Leindl, N. A. Labzoffsky, Can. J. Microbiol. 8:545 [1962] to establish "expected titers". Assays were then performed as described in Examples 1 and 2 and the following results were obtained:

| Sample | Expected Titer | Antigen Sample | Control Sample | Δ |
|---|---|---|---|---|
| Cal I | 512 | 147 | 35 | 112 |
| I | 512 | 171 | 40 | 131 |
| II | 256 | 101 | 28 | 73 |
| II | 256 | 101 | 28 | 73 |
| III | 64 | 65 | 20 | 45 |
| III | 64 | 45 | 21 | 24 |
| IV | 16 | 36 | 20 | 16 |
| IV | 16 | 33 | 19 | 14 |
| Nassau 1 | 16 | 84 | 72 | 12 |
| 2 | 16 | 41 | 17 | 24 |
| 3 | 16 | 53 | 35 | 18 |
| 4 | 64 | 65 | 26 | 39 |
| 5 | 64 | 100 | 28 | 72 |
| 6 | 64 | 74 | 29 | 45 |
| 7 | 256 | 109 | 36 | 73 |
| 8 | 256 | 112 | 30 | 82 |
| 9 | 256 | 112 | 28 | 84 |
| 10 | 1024 | 91 | 38 | 53 |
| 11 | 1024 | 100 | 57 | 43 |
| 12 | 1024 | 81 | 30 | 51 |
| 13 | 4096 | 87 | 27 | 60 |
| 14 | 4096 | 234 | 51 | 183 |
| 15 | 4096 | 104 | 34 | 70 |
| 16 | 16384 | 205 | 24 | 181 |

In the preceding description of the invention, a new two-surface method for performing immunoassays is described and in all examples the method is illustrated as a fluoro immunoassay. It should be understood, however, that in the broader applications of the invention, this novel two-surface method can be performed using radio immunoassay (RIA) and enzyme immunoassay techniques. Thus, a rubella immunoassay may be performed as described in Examples 1 and 2 with an antibody tagged with a radioactive tag instead of a fluorescent tag and the final surfaces measured by a radiation counter instead of a fluorometer. There is an important difference where radioactive tagging is employed. The two surfaces which are both exposed to the serum sample are not mounted on a single sampler as described in Example 4 because of the potential for radiation from one surface influencing the measurement of radiation from the other surface. Conceivably a two-surface sampler for RIA could be devised with sufficient shielding or spacial separation between the surfaces, but provision of both test surfaces on a single sampler is not as practical in a RIA test as in a fluorescent test.

Where the two-surface method is used with enzyme immunoassay, it may be necessary to process the two surfaces in different aliquots of the same serum to prevent interfering reactions, but in certain circumstances, it may be practical to process a two-surface enzyme immunoassay sampler in just the same way as the sampler is processed in the examples indicated above. Apart from these differences between FIA, RIA and EIA, the new two-surface method may be used in all three cases where the two surfaces react differently to the serum, one surface reacting with a broad spectrum of components excluding the desired component, so that the two different surfaces are contacted with the same serum and a quantitative measure obtained for a particular antibody as the difference in measurements between the two surfaces.

What is claimed is:

1. An immunofluorescence method of testing for the presence of an analyte where a test sample may contain an unknown amount of an interfering material which comprises preparing a first surface having bound thereto an antigen for the analyte with which the interfering material may interfere, preparing a second surface which is adapted to bind a broad spectrum of protein materials including said interfering materials but which does not bind any substantial amount of said analyte, performing an immunoassay of an unknown serum sample with said first and second surfaces by (a) immersing said first surface in an aliquot of said unknown serum, (b) immersing said first surface in an aliquot of a fluorescent labeled material adapted to bind to antibodies in the serum sample, (c) immersing the second surface in an aliquot of said unknown serum, (d) immersing said second surface in an aliquot of a fluorescent labeled material adapted to bind to antibodies in the serum sample, and thereafter measuring the difference in the amount of labeled material on the first and second surfaces.

2. An imminofluorescence method for the detection of an analyte in serum in the presence of interfering sera constituents comprising:

(a) providing two test surfaces each nonreactive with the analyte but capable of binding a broad spectrum of serum components;

(b) binding an antigen for the analyte on only one of the surfaces;

(c) moving the test surfaces through an aliquot of serum to be tested and a fluorescent labeled material;

(d) measuring quantitatively the fluorescence of each surface and subtracting the measurement of one of the surfaces from the other surface measurement to provide an analyte specific fluorescent measurement.

3. The method of claim 2 in which the test surfaces are of a polymeric material.

4. The method of claim 2 in which the antigen is a virus antigen.

5. The method of claim 4 in which the antigen is a rubella virus antigen.

6. The method of claim 4 in which the antigen is a cytomegalovirus antigen.

7. The method of claim 4 in which the antigen is a Herpes simplex virus antigen.

8. The method of claim 2 in which the antigen is a bacterial antigen.

9. The method of claim 8 in which the antigen is the antigen from *Treponema pallidum*.

10. The method of claim 2 in which the antigen is an antigen from a parasitic organism.

11. The method of claim 10 in which the antigen is an antigen from *Toxoplasma gondii*.

12. A method of claim 2 in which the fluorescent labeled material is an anti-human immunoglobulin.

13. The method of claim 12 in which the anti-human immunoglobulin is Immunoglobulin M.

14. The method of claim 2 in which the test surfaces are mounted on a single sampler.

* * * * *